US011723991B2

(12) United States Patent
Barnett

(10) Patent No.: US 11,723,991 B2
(45) Date of Patent: *Aug. 15, 2023

(54) RADIOPHARMACEUTICAL COMPOSITIONS

(71) Applicant: SERAC HEALTHCARE LIMITED, London (GB)

(72) Inventor: David Jonathan Barnett, Stevenage (GB)

(73) Assignee: SERAC HEALTHCARE LIMITED, London (GB)

( * ) Notice: Subject to any disclaimer, the term of this patent is extended or adjusted under 35 U.S.C. 154(b) by 196 days.

This patent is subject to a terminal disclaimer.

(21) Appl. No.: 16/992,917

(22) Filed: Aug. 13, 2020

(65) Prior Publication Data

US 2021/0060189 A1   Mar. 4, 2021

Related U.S. Application Data

(63) Continuation of application No. 13/811,936, filed as application No. PCT/EP2011/062897 on Jul. 27, 2011, now Pat. No. 10,758,635.

(60) Provisional application No. 61/367,992, filed on Jul. 27, 2010.

(51) Int. Cl.
*A61K 51/08* (2006.01)
*A61K 51/04* (2006.01)

(52) U.S. Cl.
CPC ........ *A61K 51/088* (2013.01); *A61K 51/0478* (2013.01); *A61K 51/082* (2013.01)

(58) Field of Classification Search
None
See application file for complete search history.

(56) References Cited

U.S. PATENT DOCUMENTS

| 4,451,451 | A  | 5/1984  | Rimmer        |
| 7,914,768 | B2 | 3/2011  | Storey et al. |
| 2004/0057899 | A1 | 3/2004 | Forster et al. |
| 2005/0063902 | A1 | 3/2005 | Storey et al. |
| 2007/0020177 | A1 | 1/2007 | McGill et al. |
| 2009/0155167 | A1 | 6/2009 | Powell et al. |

FOREIGN PATENT DOCUMENTS

| CN | 1484534     | 3/2004  |
| CN | 1708322     | 12/2005 |
| CN | 1767859     | 5/2006  |
| CN | 101282747   | 10/2008 |
| CN | 100509061   | 7/2009  |
| EP | 0122338     | 10/1984 |
| EP | 2598175     | 6/2013  |
| JP | 2004509848  | 4/2004  |
| WO | 01/97862    | 12/2001 |
| WO | 03/006491   | 1/2003  |
| WO | 2003/006070 | 1/2003  |
| WO | 2004/037297 | 5/2004  |
| WO | 2006036071  | 4/2006  |
| WO | 2009037336  | 3/2009  |
| WO | 2012013701  | 2/2012  |

OTHER PUBLICATIONS

English Translation of Decision on Rejection issued in CN201710610326.X, dated Mar. 30, 2021.
International Preliminary Report on Patentability Received for PCT Patent Application No. PCT/EP2011/062897, dated Feb. 7, 2013, 6 Pages.
International Search Report and Written Opinion Patentability Received for PCT Patent Application No. PCT/EP2011/062897, dated Nov. 21, 2011.
Office Action Received for Japanese Patent Application No. 2013-521126, dated Apr. 18, 2017.
Office Action for India Patent Appl. No. 1288/DELNP/2013, dated Nov. 21, 2017, 5 pages.
Berger, Ralf "Radical Scavengers and the Stability of 99mTc-Radiopharmaceuticals", The International Journal of Applied Radiation and Isotopes, vol. 33, Issue—12, 1982, pp. 1341-1344.
Saha, Gopal "Radiopharmaceuticals and Methods of Radiolabeling", Fundamentals of Nuclear Pharmacy, 5th Edition, Chapter 6, 2004, {pp. 80-108), 35 Pages.
Meisner et al. "A Method For Stabilizing Technetium-99m Examelazime Prepared From a Commercial Kit", European Journal of Nuclear Medicine, Aug. 1993, vol. 20, Issue—8, pp. 661-666.
Liu et al. "Ascorbic Acid: Useful as a Buffer Agent and Radiolytic Stabilizer for Melalloradiopharmaceuticals", Bioconjugate Chem., Issue—14, 2003, pp. 1052-1056.
David Edwards et al., 99mTc-NC100692—A Tracer for Imaging Vitronectin Receptors Associated with Angiogenesis: A Preclinical Investigation, Nuclear Medicine and Biology., Apr. 2008, vol. 35, No. 3, pp. 365-375.
Hua et al. Noninvasive imaging of angiogenesis with a 99mTc-labeled peptide targeted at alphavbeta3 integrin after murine hindlimb ischemia. 2005 Circulation 111: 3255-3260.
Axelsson et al. An open-label, multicenter, phase 2a study to assess the feasibility of imaging metastases in late-stage cancer patients with the alpha v beta 3-selective angiogenesis imaging agent 99mTc-NC100692. 2010 Acta. Radiol. 51: 40-46. Published Feb. 2010.
Entry for "vial". Thefreedictionary.com online dictionary. <http://medical-dictionary.thefreedictionary.com/p/vial>. Accessed Sep. 30, 2014.

(Continued)

*Primary Examiner* — Jennifer Lamberski
(74) *Attorney, Agent, or Firm* — Meunier Carlin & Curfman LLC

(57) ABSTRACT

The present invention relates to $^{99m}$Tc-maraciclatide radiopharmaceutical compositions, which are stabilised with a radioprotectant. Also described are kits for the preparation of the radiopharmaceutical compositions, as well as methods of preparing such compositions from the kit. The invention also includes methods of imaging the mammalian body using the radiopharmaceutical compositions.

18 Claims, No Drawings

(56) References Cited

OTHER PUBLICATIONS

Bach-Gansmo et al. Integrin receptor imaging of breast cancer: a proof-of-concept study to evaluate 99mTc-NC100692. 2006 J. Nucl. Med. 47: 1434-1439.
Roed et al. Metabolism in rats of NC100692, an RGD-peptide for imaging of angiogenesis. 2008 J. Pharm. Biomed. Anal. 47: 164-169.
English Translation of Chinese Office Action issued in CN 201710610326.X, dated Dec. 4, 2019.
English Translation of Chinese Office Action issued in CN 201710610326.X, dated Jul. 29, 2020.

RADIOPHARMACEUTICAL COMPOSITIONS

This application is a continuation of U.S. application Ser. No. 13/811,936, now U.S. Pat. No. 10,758,635, filed Jan. 24, 2013, as an application under 35 U.S.C. 371 of international application number PCT/EP2011/062897, filed Jul. 27, 2011, which claims priority to U.S. application No. 61/367,992 filed Jul. 27, 2010, the entire disclosures of each are hereby incorporated by reference.

FIELD OF THE INVENTION

The present invention relates to $^{99m}$Tc-maraciclatide radiopharmaceutical compositions, which are stabilised with a radioprotectant. Also described are kits for the preparation of the radiopharmaceutical compositions, as well as methods of preparing such compositions from the kit. The invention also includes methods of imaging the mammalian body using the radiopharmaceutical compositions.

BACKGROUND TO THE INVENTION $^{99m}$Tc-maraciclatide is the recommended INN (USA Approved Name) for $^{99m}$Tc-NC100692. $^{99m}$Tc-NC100692 has been described in both patents and publications, as a radiopharmaceutical which targets integrin receptors in vivo.

WO 03/006491 discloses compounds of Formula (I):

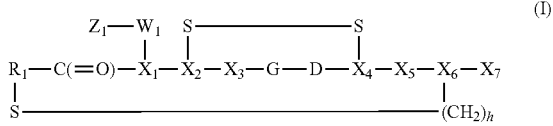

or pharmaceutically acceptable salt thereof
wherein:

G represents glycine

D represents aspartic acid $R_1$ represents —$(CH_2)_n$— or —$(CH_2)_n$—$C_6H_4$— wherein n represents a positive integer 1 to 10, h represents a positive integer 1 or 2, $X_1$ represents an amino acid residue wherein said amino acid possesses a functional side-chain such as an acid or amine, $X_2$ and $X_4$ represent independently an amino acid residue capable of forming a disulfide bond, $X_3$ represents arginine, N-methylarginine or an arginine mimetic, $X_5$ represents a hydrophobic amino acid or derivatives thereof, $X_6$ represents a thiol-containing amino acid residue, $X_7$ is absent or represents a biomodifier moiety, $Z_1$ represents an anti-neoplastic agent, a chelating agent or a reporter moiety and $W_1$ is absent or represents a spacer moiety.

WO 03/006491 discloses that a preferred chelating moiety has the formula shown, and includes $^{99m}$Tc complexes of said chelator conjugate of Formula I therein:

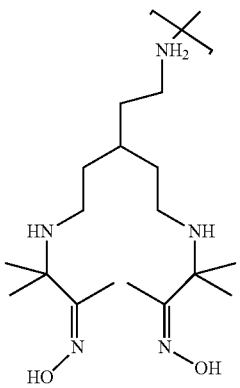 [SMILES: CNCCC(CCNC(C)(C)/C(C)=N\O)CCNC(C)(C)/C(C)=N\O]

WO 03/006491 does not disclose kits.

Edwards et al [Nucl. Med. Biol., 35, 365-375 (2008)] disclose that $^{99m}$Tc-maraciclatide ($^{99m}$Tc-NC100692) can be prepared from a kit. Edwards et al state that each lyophilised kit contains approximately 44 nmol maraciclatide (NC100692), plus a number of excipients including buffer, stannous reducing agent and methylene diphosphonic acid (present as a $Sn^{2+}$ solubiliser). Edwards et al report that the radiochemical purity (RCP) of each reconstituted kit was determined at 20 minutes post reconstitution, and was found to be at least 90%. The RCP was found to be stable over the period that the reconstituted kits were used.

THE PRESENT INVENTION

Technetium-99m ($^{99m}$Tc) is a radioisotope which decays with a half-life of 6.02 hours to technetium-99 ($^{99}$Tc). The radioactive decay is accompanied by the emission of a gamma ray with an energy that is near ideal for medical imaging with a modern gamma-camera. The decay product, $^{99}$Tc, is also radioactive and decays by β-emission with a half-life of $2.1 \times 10^5$ years (to the stable isotope $^{99}$Ru), but the radioactive emissions from $^{99}$Tc are insufficient for medical imaging.

Conventional $^{99m}$Tc "generators" comprise the radioisotope $^{99}$Mo, which decays with a half-life of 66.2 hours. The chemical form of the technetium eluted from such a generator is $^{99m}$Tc-pertechnetate. About 86% of $^{99}$Mo decays result in the production of $^{99m}$Tc, however ca. 14% of $^{99}$Mo decays result in the direct production of $^{99}$Tc. Therefore, if a $^{99m}$Tc generator is eluted a very short time after the previous elution, the $^{99m}$Tc content will be low but will be about 86% of the total technetium content. As time passes since the previous elution of the generator, $^{99}$Tc is being produced both from $^{99}$Mo and from the decay of $^{99m}$Tc to $^{99}$Tc. Consequently, as the time interval between generator elutions increases, the $^{99}$Tc/$^{99m}$Tc ratio increases. The $^{99}$Tc and $^{99m}$Tc technetium isotopes are chemically identical, and consequently any radiopharmaceutical preparation must be able to cope with a wide range of $^{99}$Tc chemical content in the eluate in order to be able to function effectively over the usable lifetime of the generator. It is also the case that elutions made with a fresh $^{99m}$Tc generator are likely to have a higher radioactive concentration, and thus have a higher concentration of reactive free radicals arising from radiolysis of the solvent (water). A viable $^{99m}$Tc radiopharmaceutical preparation thus needs to be able to provide satisfactory RCP performance even when such reactive free radicals are present. These characteristics of the $^{99m}$Tc generator are illustrated in most radiochemistry or nuclear chemistry textbooks, and the problems that different eluate properties can give to the performance of $^{99m}$Tc kits have been described by Saha, G. B. "*Radiopharmaceuticals and Methods of Radiolabeling*"; Chapter 6 (pages 80-108) in Fundamentals of Nuclear Pharmacy (3$^{rd}$ Edn.).

The present inventors have found that the Maraciclatide kit reported by Edwards et al (above) suffers from various problems not previously recognised in the prior art:
 (i) relatively low initial RCP post-reconstitution of the kit with $^{99m}$Tc-pertechnetate;
 (ii) insufficient post-reconstitution stability;
 (iii) the need to store and ship the kit at −15 to −20° C. to maintain kit stability and performance;
 (iv) only a single patient dose being obtainable from the kit.

The present invention provides improved $^{99m}$Tc-maraciclatide radiopharmaceutical compositions which exhibit more reproducible initial radiochemical purity (RCP) and improved stability post-reconstitution, so that an RCP of 85 to 90% is maintained at 6 hours post-reconstitution. The problem of unsatisfactory RCP for $^{99m}$Tc-maraciclatide preparations under certain conditions of radioactivity levels, radioactive concentrations or reconstitution volumes was not recognised in the prior art. Such conditions are those that could arise under normal conditions of use of a commercial radionuclide generator, such as a $^{99m}$Tc generator.

Berger [Int. J. Appl. Rad. Isotop., 33, 1341-1344 (1982)] discloses that a wide range of antioxidants can be used to stabilise $^{99m}$Tc-radiopharmaceuticals. Methylene Blue and ascorbic acid have since been highlighted as particularly suitable stabilisers [Weisner et al, Eur. J. Nucl. Med., 20, 661-666 (1993) and Liu et al, Bioconj. Chem., 14(4), 1052-1056 (2003)].

The present inventors have also established that the well-known radioprotectant ascorbic acid/ascorbate actually has a deleterious effect on the RCP of $^{99m}$Tc-maraciclatide.

A further known radioprotectant gentisic acid caused discolouration problems which negated its use in the present composition. The present invention provides compositions comprising a radioprotectant which solve this previously unrecognised problem. The kits of the present invention have the advantages of: higher initial RCP; more robust RCP over longer time periods post-reconstitution; compatibility with various commercial $^{99m}$Tc radiopharmaceutical generators and under a range of elution conditions; the facility to obtain two patient doses per kit (i.e. to reconstitute successfully with higher levels of radioactivity); adequate stability to be stored and shipped at fridge (+5±3° C.) rather than freezer temperature (−10 to −20° C.) and kit shelf-life stability of at least 3 years.

DETAILED DESCRIPTION OF THE INVENTION

In a first aspect, the present invention provides a radiopharmaceutical composition which comprises:
 (i) $^{99m}$Tc-maraciclatide;
 (ii) a radioprotectant chosen from para-aminobenzoic acid or a salt thereof with a biocompatible cation;
 in a biocompatible carrier in a form suitable for mammalian administration.

The term "maraciclatide" refers to the compound known in the scientific literature as NC100692 [D. Edwards et al, Nucl. Med. Biol., 35, 365-375 (2008)]. The chemical name is: 1,5-pentanedioic acid-(5-[2-hydroxyimino-1,1-dimethyl-propylamino]-3-(2-[2-hydroxyimido-1,1-dimethyl-propylamino]-ethyl)-pentyl)-amide 5-[13-benzyl-19-carboxymethyl-25-(3-guanidino-propyl)-10-(4,7,10,16-tetraoxa-14,18-dioxo-1,13,19-triazanonadecyl)-carbamoyl-3,6,12,15,18,21,24,27-octaoxo-8,29,30-trithia-2,5,11,14,17,20,23,26-octaaza-bicyclo[14.11.4]hentriacont-4-yl] pentyl-amide. The chemical structure of maraciclatide is as follows:

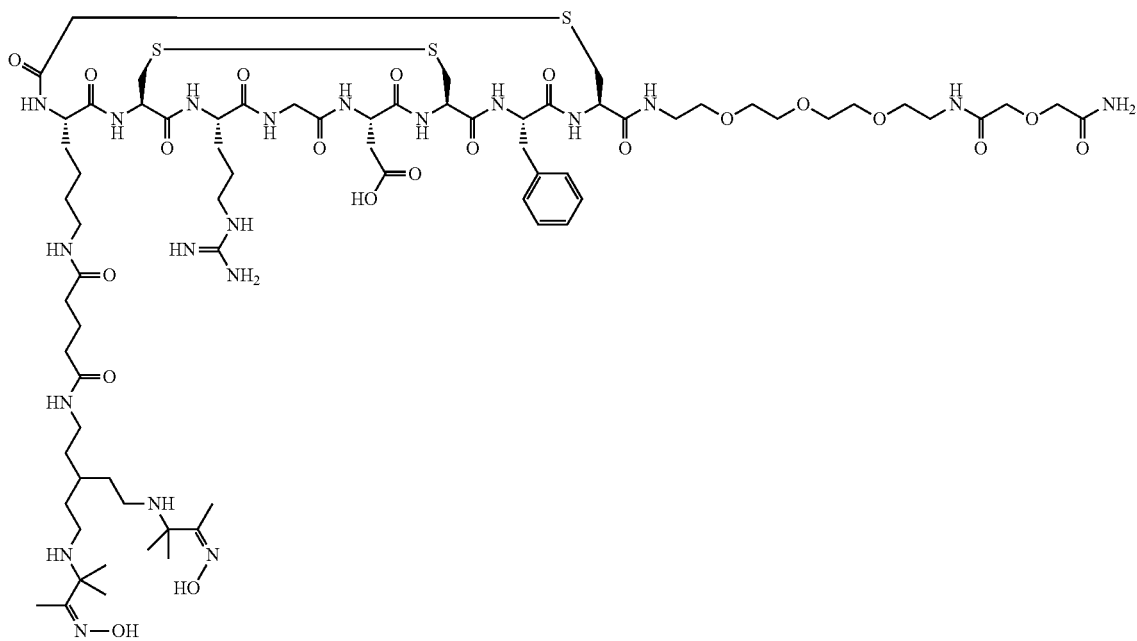 [SMILES: C/C(=N/O)C(C)(C)NCCC(CCNC(=O)CCCC(=O)NCCCC[C@@H]1NC(=O)CSC[C@@H](C(=O)NCCOCCOCCOCCNC(=O)COCC(N)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2)CCNC(C)(C)/C(C)=N\O]

Maraciclatide

Maraciclatide can be used in the free base form, or in the salt form (eg. the trifluoroacetate).

The term "radiopharmaceutical" has its conventional meaning, and refers to a radioactive compound suitable for in vivo mammalian administration for use in diagnosis or therapy.

By the term "radioprotectant" is meant a compound which inhibits degradation reactions, such as redox processes, by trapping highly-reactive free radicals, such as oxygen-containing free radicals arising from the radiolysis of water. The radioprotectant of the present invention is suitably chosen from para-aminobenzoic acid (i.e. 4-aminobenzoic acid) and salts thereof with a biocompatible cation. These radioprotectants are commercially available, including in pharmaceutical grade purity. Preferably, pharmaceutical grade material is used.

By the term "biocompatible cation" ($B^c$) is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium.

The "biocompatible carrier" is a fluid, especially a liquid, in which the radiopharmaceutical can be suspended or preferably dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). Preferably the biocompatible carrier is pyrogen-free water for injection, isotonic saline or phosphate buffer.

By the phrase "in a form suitable for mammalian administration" is meant a composition which is sterile, pyrogen-free, lacks compounds which produce toxic or adverse effects, and is formulated at a biocompatible pH (approximately pH 4.0 to 10.5, preferably 6.5 to 9.5 for the agents of the present invention) and physiologically compatible osmolality. Such compositions lack particulates which could risk causing emboli in vivo, and are formulated so that precipitation does not occur on contact with biological fluids (e.g. blood). Such compositions also contain only biologically compatible excipients, and are preferably isotonic.

Preferably, the mammal is an intact mammalian body in vivo, and is more preferably a human subject. Preferably, the radiopharmaceutical can be administered to the mammalian body in a minimally invasive manner, i.e. without a substantial health risk to the mammalian subject even when carried out under professional medical expertise. Such minimally invasive administration is preferably intravenous administration into a peripheral vein of said subject, without the need for local or general anaesthetic.

The term "comprising" has its conventional meaning throughout this application and implies that the composition must have the components listed, but that other, unspecified compounds or species may be present in addition. The term 'comprising' includes as a preferred subset "consisting essentially of" which means that the composition has the components listed without other compounds or species being present.

The radiopharmaceutical composition may contain additional optional excipients such as: an antimicrobial preservative, pH-adjusting agent, filler, solubiliser or osmolality adjusting agent.

By the term "antimicrobial preservative" is meant an agent which inhibits the growth of potentially harmful micro-organisms such as bacteria, yeasts or moulds. The antimicrobial preservative may also exhibit some bactericidal properties, depending on the dosage employed. The main role of the antimicrobial preservative(s) of the present invention is to inhibit the growth of any such microorganism in the pharmaceutical composition. The antimicrobial preservative may, however, also optionally be used to inhibit the growth of potentially harmful micro-organisms in one or more components of kits used to prepare said composition prior to administration. Suitable antimicrobial preservative(s) include: the parabens, i.e. methyl, ethyl, propyl or butyl paraben or mixtures thereof; benzyl alcohol; ethanol, phenol; cresol; cetrimide and thiomersal. Preferred antimicrobial preservative(s) are the parabens or ethanol.

The term "pH-adjusting agent" means a compound or mixture of compounds useful to ensure that the pH of the composition is within acceptable limits (approximately pH 4.0 to 10.5, preferably 6.5 to 9.5 for the agents of the present invention) for human or mammalian administration. Suitable such pH-adjusting agents include pharmaceutically acceptable buffers, such as tricine, phosphate, acetate or TRIS [i.e. tris(hydroxymethyl)aminomethane], and pharmaceutically acceptable bases such as sodium carbonate, sodium bicarbonate or mixtures thereof. When the composition is employed in kit form, the pH adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

By the term "solubiliser" is meant an additive present in the composition which increases the solubility of the radiopharmaceutical in the solvent. A preferred such solvent is aqueous media, and hence the solubiliser preferably improves solubility in water. Suitable such solubilisers include: $C_{1-4}$ alcohols; glycerine; polyethylene glycol (PEG); propylene glycol; polyoxyethylene sorbitan monooleate; sorbitan monooloeate; polysorbates (e.g. Tween™); poly(oxyethylene)poly(oxypropylene)poly(oxyethylene) block copolymers (Pluronics™); cyclodextrins (e.g. alpha, beta or gamma cyclodextrin, hydroxypropyl-β-cyclodextrin or hydroxypropyl-γ-cyclodextrin) and lecithin.

Preferred solubilisers are cyclodextrins, $C_{1-4}$ alcohols, polysorbates and Pluronics™, more preferably cyclodextrins and $C_{2-4}$ alcohols. When the solubiliser is an alcohol, it is preferably ethanol or propanol, more preferably ethanol. Ethanol has potentially several roles, since it can also function as a biocompatible carrier, radioprotectant or antimicrobial preservative. When the solubiliser is a cyclodextrin, it is preferably a gamma cyclodextrin, more preferably hydroxypropyl-β-cyclodextrin (HPCD). The concentration of cyclodextrin can be from about 0.1 to about 40 mg/ml, preferably between about 5 and about 35 mg/ml, more preferably 20 to 30 mg/ml, most preferably around 25 mg/ml.

Preferred Features.

The radioprotectant of the present invention preferably comprises sodium para-aminobenzoate. An additional radioprotectant may also be present. If such an additional radioprotectant is used, it preferably does not comprise ascorbic acid or gentisic acid or salts thereof. More preferably, the radioprotectant of the present invention consists essentially of para-aminobenzoic acid or a salt thereof with a biocompatible cation. Most preferably, the radioprotectant of the present invention consists essentially of sodium para-aminobenzoate.

The radiopharmaceutical composition of the first aspect is suitably provided in a pharmaceutical grade container. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour. Preferred multiple dose containers comprise a single bulk vial (e.g. of 10 to 30 cm$^3$ volume) which contains multiple patient doses, whereby single patient doses can thus be withdrawn into clinical grade syringes at various time intervals during the viable lifetime of the preparation to suit the clinical situation.

The radiopharmaceutical composition of the first aspect may also be provided in a syringe. Pre-filled syringes are designed to contain a single human dose, or "unit dose" and are therefore preferably a single-use or other syringe suitable for clinical use. The radiopharmaceutical syringe is preferably provided with a syringe shield to minimise radiation dose to the operator.

In a second aspect, the present invention provides a kit for the preparation of the radiopharmaceutical composition of the first aspect, wherein said kit comprises:
(i) Maraciclatide;
(ii) a radioprotectant chosen from para-aminobenzoic acid or a salt thereof with a biocompatible cation;
(iii) a stannous reductant;
(iv) methylene diphosphonic acid or a salt thereof with a biocompatible cation.

By the term "kit" is meant one or more pharmaceutical grade containers, comprising the necessary non-radioactive chemicals to prepare the desired radiopharmaceutical composition, together with operating instructions. The kit is designed to be reconstituted with $^{99m}$Tc to give a solution suitable for human administration with the minimum of manipulation. The kit of the present invention preferably comprises a lyophilised composition containing all the kit components in a single lyophilised formulation in a single container.

The kit of the second aspect is non-radioactive. Preferred aspects of the radioprotectant in the kit are as described in the first aspect (above).

The term "stannous reductant" has its conventional meaning in the field of $^{99m}$Tc radiopharmaceutical kits, and refers to a salt of Sn$^{2+}$, ie. tin in the Sn(II) oxidation state. Suitable such salts may be in the hydrated or anhydrous form, and include: stannous chloride, stannous fluoride and stannous tartrate. A preferred such stannous reductant is stannous chloride.

The term "methylene diphosphonic acid" has its conventional chemical meaning, and has the chemical structure shown:

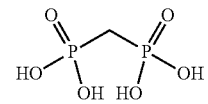

methylene diphosphonic acid (MDP)

The kit is preferably lyophilised and is designed to be reconstituted with sterile $^{99m}$Tc-pertechnetate (TcO$_4^-$) from a $^{99m}$Tc radioisotope generator to give a solution suitable for human administration without further manipulation. The non-radioactive kits may optionally further comprise additional components such as a transchelator, antimicrobial preservative, pH-adjusting agent or filler—as defined for the first aspect above.

The kit of the second aspect preferably further comprises a buffer which comprises a mixture of sodium hydrogen carbonate and anhydrous sodium carbonate.

A most preferred kit formulation is as follows (Formulation C of Example 8):

| Component | Quantity per vial |
|---|---|
| Maraciclatide | 75 μg |
| Stannous chloride dihydrate | 17.8 μg |
| Methylene diphosphonic acid (MDP) | 90 μg |
| Para-aminobenzoic acid (pABA), sodium salt | 200 μg |
| Sodium hydrogen carbonate | 1800 μg |
| Sodium carbonate anhydrous | 630 μg |

In a third aspect, the present invention provides a method of preparation of the radiopharmaceutical composition of the first aspect, which comprises either:
(i) reconstitution of the kit of the second aspect with a supply of a biocompatible carrier, followed by addition of a supply of $^{99m}$Tc in a biocompatible carrier to the reconstituted kit; or
(ii) reconstitution of the kit of the second aspect with a supply of $^{99m}$Tc in a biocompatible carrier.

Preferred aspects of the kit in the third aspect are as described in the second aspect (above).

The supply of $^{99m}$Tc is suitably in sterile form, and is preferably $^{99m}$Tc-pertechnetate (TcO$_4^-$) from a $^{99m}$Tc radioisotope generator. Such generators are commercially available.

When option (i) is used, that means first reconstituting the kit with a non-radioactive biocompatible carrier in sterile form (as defined above; e.g. saline), followed by the addition of the $^{99m}$Tc. When option (ii) is used, that means reconstituting the kit by addition of $^{99m}$Tc in a biocompatible carrier directly to the kit. Option (ii) is preferred, especially in conjunction with a single, lyophilised kit container, since that gives a solution suitable for human administration without further manipulation.

The method of the third aspect is preferably carried out at room temperature, i.e. no heating is required.

The method of the third aspect is preferably used to prepare unit patient doses, by withdrawing the radiopharmaceutical composition into a clinical grade syringe, as described in the first aspect (above).

In a fourth aspect, the present invention provides the use of the kit of the second aspect in the preparation of the radiopharmaceutical composition of the first aspect.

Preferred aspects of the kit and radiopharmaceutical composition in the fourth aspect are as described in the second and first aspects respectively (above).

In a fifth aspect, the present invention provides the use of para-aminobenzoic acid or a salt thereof with a biocompatible cation, as a radioprotectant to stabilise either:
(i) $^{99m}$Tc-maraciclatide radiopharmaceutical compositions;
(ii) kits for the preparation of $^{99m}$Tc-maraciclatide radiopharmaceutical compositions.

The radiopharmaceutical compositions and kits of the fifth aspect, and preferred embodiments thereof, are preferably as described in the first and second aspects respectively (above). Preferred embodiments of the radioprotectant in the fifth aspect are as described in the first aspect (above).

In a sixth aspect, the present invention provides the use of the radiopharmaceutical composition of the first aspect in a method of imaging of the mammalian body. Preferred aspects of the radiopharmaceutical composition in the sixth aspect are as described in the first aspect (above). Preferably, the mammal is an intact mammalian subject in vivo, and is more preferably a human subject. The method of imaging is preferably used to assist in a method of diagnosis of said mammalian subject.

In a seventh aspect, the present invention provides a method of imaging of the mammalian body which comprises imaging a mammal which had previously been administered with the radiopharmaceutical composition of the first aspect. Preferred aspects of the radiopharmaceutical composition in the seventh aspect are as described in the first aspect (above). Preferably, the mammal is an intact mammalian body in vivo, and is more preferably a human subject.

The imaging of the sixth and seventh aspects is preferably to image a mammalian subject suffering from a disease in which in which integrins are expressed, such as angiogenesis, fibrosis or inflammation.

The invention is illustrated by the non-limiting Examples detailed below. Examples 1 to 3 provide the synthesis of Chelator 1 (also sometimes called carba-Pn216) of the invention. Example 4 provides the synthesis of Chelator 1A of the invention—an active ester-functionalised version of Chelator 1. Example 5 provides the synthesis of cyclic peptides of the invention and chelator conjugation. Example 6 provides the synthesis of maraciclatide. Example 7 provides a study on the choice of radioprotectant. Example 8 provides data on optimising the amount of radioprotectant used. Example 9 describes comparative kit formulations vs a prior art kit formulation. Example 10 provides a $^{99m}$Tc generator compatibility study for kits of the invention, showing that they are compatible with a range of commercial generators under a range of conditions. Example 11 provides data on the shelf-life stability of kits of the invention.

Abbreviations.

Conventional single letter or 3-letter amino acid abbreviations are used.

Ac: Acetyl
Boc: tert-Butyloxycarbonyl
tBu: tertiary-butyl
DMF: Dimethylformamide
DMSO: Dimethylsulfoxide
Fmoc: 9-Fluorenylmethoxycarbonyl
HATU: O-(7-Azabenzotriazol-1-yl)-N,N,N',N'-tetramethyluronium hexafluorophosphate.
HBTU: O-Benzotriazol-1-yl-N,N,N',N'-tetramethyluronium hexafluorophosphate
HPLC: High performance liquid chromatography
NMM: N-Methylmorpholine
pABA: para-amino-benzoic acid sodium salt
PBS: Phosphate-buffered saline
PEG: polyethyleneglycol, repeat units of $(OCH_2CH_2)_n$, where n is an integer,
tBu: tert-butyl
RCP: radiochemical purity.
RP-HPLC: reversed-phase HPLC.
TFA: Trifluoroacetic acid
THF: Tetrahydrofuran
TIS: Triisopropylsilane
TLC: thin layer chromatography
Trt: Trityl.

Compounds of the Invention

| Compound | Structure |
|---|---|
| Chelator 1 | 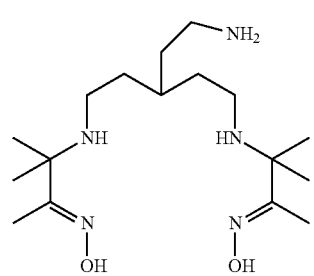 [SMILES: C/C(=N\O)C(C)(C)NCCC(CCN)CCNC(C)(C)/C(C)=N/O] |

-continued

| Compound | Structure |
|---|---|
| Chelator 1A | 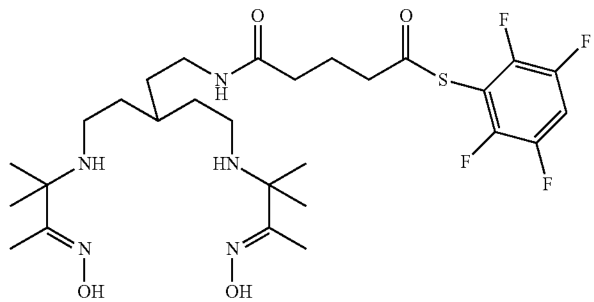 [SMILES: C/C(=N\O)C(C)(C)NCCC(CCNC(=O)CCCC(=O)Sc1c(F)c(F)cc(F)c1F)CCNC(C)(C)/C(C)=N/O] |

Example 1

Synthesis of 1,1,1-Tris(2-aminoethyl)methane

Step 1(a): 3(methoxycarbonylmethylene)glutaric acid dimethylester

Carbomethoxymethylenetriphenylphosphorane (167 g, 0.5 mol) in toluene (600 ml) was treated with dimethyl 3-oxoglutarate (87 g, 0.5 mol) and the reaction heated to 100° C. on an oil bath at 120° C. under an atmosphere of nitrogen for 36 h. The reaction was then concentrated in vacuo and the oily residue triturated with 40/60 petrol ether/diethylether (1:1, 600 ml). Triphenylphosphine oxide precipitated out and the supernatant liquid was decanted/filtered off. The residue on evaporation in vacuo was Kugelrohr distilled under high vacuum Bpt (oven temperature 180-200° C. at 0.2 torr) to give 3-(methoxycarbonylmethylene)glutaric acid dimethylester (89.08 g, 53%).

NMR $^1$H(CDCl$_3$): δ3.31 (2H, s, CH$_2$), 3.7 (9H, s, 3×OCH$_3$), 3.87 (2H, s, CH$_2$), 5.79 (1H, s, =CH,) ppm.

NMR $^{13}$C(CDCl3), δ36.56, CH$_3$, 48.7, 2×CH$_3$, 52.09 and 52.5 (2×CH$_2$); 122.3 and 146.16 C=CH; 165.9, 170.0 and 170.5 3×COO ppm.

Step 1(b): Hydrogenation of 3-(methoxycarbonylmethylene)glutaric acid dimethylester 3-(Methoxycarbonylmethylene)glutaric acid dimethylester (89 g, 267 mmol) in methanol (200 ml) was shaken with (10% palladium on charcoal: 50% water) (9 g) under an atmosphere of hydrogen gas (3.5 bar) for 30 h. The solution was filtered through kieselguhr and concentrated in vacuo to give 3-(methoxycarbonylmethyl)glutaric acid dimethylester as an oil, yield (84.9 g, 94%).

NMR $^1$H (CDCl$_3$), δ2.48 (6H, d, J=8 Hz, 3×CH$_2$), 2.78 (1H, hextet, J=8 Hz CH,) 3.7 (9H, s, 3×CH$_3$).

NMR $^{13}$C(CDCl$_3$), δ28.6, CH; 37.50, 3×CH$_3$; 51.6, 3×CH$_2$; 172.28, 3×COO.

Step 1(c): Reduction and Esterification of Trimethyl Ester to the Triacetate Under an atmosphere of nitrogen in a 3 necked 2 L round bottomed flask lithium aluminium hydride (20 g, 588 mmol) in THF (400 ml) was treated cautiously with tris(methyloxycarbonylmethyl)methane (40 g, 212 mmol) in THF (200 ml) over 1 h. A strongly exothermic reaction occurred, causing the solvent to reflux strongly. The reaction was heated on an oil bath at 90° C. at reflux for 3 days. The reaction was quenched by the cautious dropwise addition of acetic acid (100 ml) until the evolution of hydrogen ceased. The stirred reaction mixture was cautiously treated with acetic anhydride solution (500 ml) at such a rate as to cause gentle reflux. The flask was equipped for distillation and stirred and then heating at 90° C. (oil bath temperature) to distil out the THF. A further portion of acetic anhydride (300 ml) was added, the reaction returned to reflux configuration and stirred and heated in an oil bath at 140° C. for 5 h. The reaction was allowed to cool and filtered. The aluminium oxide precipitate was washed with ethyl acetate and the combined filtrates concentrated on a rotary evaporator at a water bath temperature of 50° C. in vacuo (5 mmHg) to afford an oil. The oil was taken up in ethyl acetate (500 ml) and washed with saturated aqueous potassium carbonate solution. The ethyl acetate solution was separated, dried over sodium sulfate, and concentrated in vacuo to afford an oil. The oil was Kugelrohr distilled in high vacuum to give tris(2-acetoxyethyl)methane (45.3 g, 95.9%) as an oil. Bp. 220° C. at 0.1 mmHg.

NMR $^1$H(CDCl$_3$), δ1.66 (7H, m, 3×CH$_2$, CH), 2.08 (1H, s, 3×CH$_3$); 4.1(6H, t, 3×CH$_2$O).

NMR $^{13}$C(CDCl$_3$), δ20.9, CH$_3$; 29.34, CH; 32.17, CH$_2$; 62.15, CH$_2$O; 171, CO.

Step 1(d): Removal of Acetate Groups from the Triacetate

Tris(2-acetoxyethyl)methane (45.3 g, 165 mM) in methanol (200 ml) and 880 ammonia (100 ml) was heated on an oil bath at 80° C. for 2 days. The reaction was treated with a further portion of 880 ammonia (50 ml) and heated at 80° C. in an oil bath for 24 h. A further portion of 880 ammonia (50 ml) was added and the reaction heated at 80° C. for 24 h. The reaction was then concentrated in vacuo to remove all solvents to give an oil. This was taken up into 880 ammonia (150 ml) and heated at 80° C. for 24 h. The reaction was then concentrated in vacuo to remove all solvents to give an oil. Kugelrohr distillation gave acetamide bp 170-180 0.2 mm. The bulbs containing the acetamide were washed clean and the distillation continued. Tris(2-hydroxyethyl)methane (22.53 g, 92%) distilled at bp 220° C. 0.2 mm.

NMR $^1$H(CDCl$_3$), δ1.45(6H, q, 3×CH$_2$), 2.2(1H, quintet, CH); 3.7(6H, t 3×CH$_2$OH); 5.5(3H, brs, 3×OH).

NMR $^{13}$C(CDCl$_3$), δ22.13, CH; 33.95, 3×CH$_2$; 57.8, 3×CH$_2$OH.

Step 1(e): Conversion of the Triol to the Tris(Methanesulfonate)

To an stirred ice-cooled solution of tris(2-hydroxyethyl) methane (10 g, 0.0676 mol) in dichloromethane (50 ml) was slowly dripped a solution of methanesulfonyl chloride (40 g, 0.349 mol) in dichloromethane (50 ml) under nitrogen at such a rate that the temperature did not rise above 15° C. Pyridine (21.4 g, 0.27 mol, 4 eq) dissolved in dichloromethane (50 ml) was then added drop-wise at such a rate that the temperature did not rise above 15° C., exothermic reaction.

The reaction was left to stir at room temperature for 24 h and then treated with 5N hydrochloric acid solution (80 ml) and the layers separated. The aqueous layer was extracted with further dichloromethane (50 ml) and the organic extracts combined, dried over sodium sulfate, filtered and concentrated in vacuo to give tris[2-(methylsulfonyloxy)ethyl] methane contaminated with excess methanesulfonyl chloride. The theoretical yield was 25.8 g.

NMR $^1$H(CDCl$_3$), δ4.3 (6H, t, 2×CH$_2$), 3.0 (9H, s, 3×CH$_3$), 2 (1H, hextet, CH), 1.85 (6H, q. 3×CH$_2$).

Step 1(f): Preparation of 1,1,1-tris(2-azidoethyl)methane

A stirred solution of tris[2-(methylsulfonyloxy)ethyl] methane [from Step 1(e), contaminated with excess methylsulfonyl chloride] (25.8 g, 67 mmol, theoretical) in dry DMF (250 ml) under nitrogen was treated with sodium azide (30.7 g, 0.47 mol) portion-wise over 15 minutes. An exotherm was observed and the reaction was cooled on an ice bath. After 30 minutes, the reaction mixture was heated on an oil bath at 50° C. for 24 h. The reaction became brown in colour. The reaction was allowed to cool, treated with dilute potassium carbonate solution (200 ml) and extracted three times with 40/60 petrol ether/diethylether 10:1 (3×150 ml). The organic extracts were washed with water (2×150 ml), dried over sodium sulfate and filtered. Ethanol (200 ml) was added to the petrol/ether solution to keep the triazide in solution and the volume reduced in vacuo to no less than 200 ml. Ethanol (200 ml) was added and reconcentrated in vacuo to remove the last traces of petrol leaving no less than 200 ml of ethanolic solution. The ethanol solution of triazide was used directly in Step 1(g).

CARE: DO NOT REMOVE ALL THE SOLVENT AS THE AZIDE IS POTENTIALLY EXPLOSIVE AND SHOULD BE KEPT IN DILUTE SOLUTION AT ALL TIMES.

Less than 0.2 ml of the solution was evaporated in vacuo to remove the ethanol and an NMR run on this small sample: NMR $^1$H(CDCl$_3$), δ3.35 (6H, t, 3×CH$_2$), 1.8 (1H, septet, CH,), 1.6 (6H, q, 3×CH$_2$).

Step 1(g): Preparation of 1,1,1-tris(2-aminoethyl)methane

Tris(2-azidoethyl)methane (15.06 g, 0.0676 mol), (assuming 100% yield from previous reaction) in ethanol (200 ml) was treated with 10% palladium on charcoal (2 g, 50% water) and hydrogenated for 12 h. The reaction vessel was evacuated every 2 hours to remove nitrogen evolved from the reaction and refilled with hydrogen. A sample was taken for NMR analysis to confirm complete conversion of the triazide to the triamine.

Caution: unreduced azide could explode on distillation. The reaction was filtered through a celite pad to remove the catalyst and concentrated in vacuo to give tris(2-aminoethyl) methane as an oil. This was further purified by Kugelrohr distillation bp. 180-200° C. at 0.4 mm/Hg to give a colourless oil (8.1 g, 82.7% overall yield).

NMR $^1$H(CDCl$_3$), δ2.72 (6H, t, 3×CH$_2$N), 1.41 (H, septet, CH), 1.39 (6H, q, 3×CH$_2$).

NMR $^{13}$C(CDCl$_3$), δ39.8 (CH$_2$NH$_2$), 38.2 (CH$_2$), 31.0 (CH).

Example 2

Preparation of 3-chloro-3-methyl-2-nitrosobutane

A mixture of 2-methylbut-2-ene (147 ml, 1.4 mol) and isoamyl nitrite (156 ml, 1.16 mol) was cooled to −30° C. in a bath of cardice and methanol and vigorously stirred with an overhead air stirrer and treated dropwise with concentrated hydrochloric acid (140 ml, 1.68 mol) at such a rate that the temperature was maintained below −20° C. This requires about 1 h as there is a significant exotherm and care must be taken to prevent overheating. Ethanol (100 ml) was added to reduce the viscosity of the slurry that had formed at the end of the addition and the reaction stirred at −20 to −10° C. for a further 2 h to complete the reaction. The precipitate was collected by filtration under vacuum and washed with 4×30 ml of cold (−20° C.) ethanol and 100 ml of ice cold water, and dried in vacuo to give 3-chloro-3-methyl-2-nitrosobutane as a white solid. The ethanol filtrate and washings were combined and diluted with water (200 ml) and cooled and allowed to stand for 1 h at −10° C. when a further crop of 3-chloro-3-methyl-2-nitrosobutane crystallised out. The precipitate was collected by filtration and washed with the minimum of water and dried in vacuo to give a total yield of 3-chloro-3-methyl-2-nitrosobutane (115 g 0.85 mol, 73%)>98% pure by NMR.

NMR $^1$H(CDCl$_3$), As a mixture of isomers (isomer1, 90%) 1.5 d, (2H, CH$_3$), 1.65 d, (4H, 2×CH$_3$), 5.85, q, and 5.95, q, together 1H. (isomer2, 10%), 1.76 s, (6H, 2×CH$_3$), 2.07(3H, CH$_3$).

Example 3

Synthesis of bis[N-(1,1-dimethyl-2-N-hydroxyimine propyl)2-aminoethyl]-(2-aminoethyl)methane (Chelator 1)

To a solution of tris(2-aminoethyl)methane (Example 1; 4.047 g, 27.9 mmol) in dry ethanol (30 ml) was added potassium carbonate anhydrous (7.7 g, 55.8 mmol, 2 eq) at room temperature with vigorous stirring under a nitrogen atmosphere. A solution of 3-chloro-3-methyl-2-nitrosobutane (Example 2; 7.56 g, 55.8 mol, 2 eq) was dissolved in dry ethanol (100 ml) and 75 ml of this solution was dripped slowly into the reaction mixture. The reaction was followed by TLC on silica [plates run in dichloromethane, methanol, concentrated (0.88 sg) ammonia; 100/30/5 and the TLC plate developed by spraying with ninhydrin and heating]. The mono-, di- and tri-alkylated products were seen with RF's increasing in that order. Analytical HPLC was run using PRP reverse phase column in a gradient of 7.5-75% acetonitrile in 3% aqueous ammonia. The reaction was concentrated in vacuo to remove the ethanol and re-suspended in water (110 ml). The aqueous slurry was extracted with ether (100 ml) to remove some of the trialkylated compound and lipophilic impurities leaving the mono and desired dialkylated product in the water layer. The aqueous solution was buffered with ammonium acetate (2 eq, 4.3 g, 55.8 mmol) to ensure good chromatography. The aqueous solution was stored at 4° C. overnight before purifying by automated preparative HPLC.

Yield (2.2 g, 6.4 mmol, 23%).
Mass spec; Positive ion 10 V cone voltage. Found: 344; calculated M+H=344.

NMR $^1$H(CDCl$_3$), δ1.24(6H, s, 2×CH$_3$), 1.3(6H, s, 2×CH$_3$), 1.25-1.75(7H. m, 3×CH$_2$, CH), (3H, s, 2×CH$_2$), 2.58 (4H, m, CH$_2$N), 2.88(2H, t CH$_2$N), 5.0 (6H, s, NH$_2$, 2×NH, 2×OH).

NMR $^1$H ((CD$_3$)$_2$SO) δ1.1 4×CH; 1.29, 3×CH$_2$; 2.1 (4H, t, 2×CH$_2$);
NMR $^{13}$C((CD$_3$)$_2$SO), δ9.0 (4×CH$_3$), 25.8 (2×CH$_3$), 31.0 2×CH$_2$, 34.6 CH$_2$, 56.8 2×CH$_2$N; 160.3, C═N.

HPLC conditions: flow rate 8 ml/min using a 25 mm PRP column [A=3% ammonia solution (sp.gr=0.88)/water; B=Acetonitrile].

|  |  | Time (min) | | | | |
| --- | --- | --- | --- | --- | --- | --- |
|  |  | 0 | 15 | 20 | 22 | 30 |
| Gradient | % B | 7.5 | 75.0 | 75.0 | 7.5 | 7.5 |

Load 3 ml of aqueous solution per run, and collect in a time window of 12.5-13.5 min.

Example 4

Synthesis of Tetrafluorothiophenyl ester of Chelator 1-glutaric acid (Chelator 1A)

(Step 4a) Synthesis of [Chelator 1]-glutaric acid intermediate

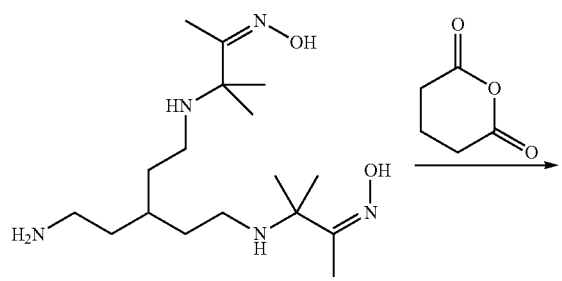

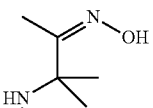

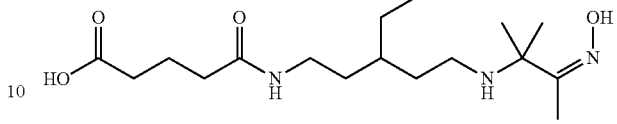

Chelator 1 (100 mg, 0.29 mmol) was dissolved in DMF (10 ml) and glutaric anhydride (33 mg, 0.29 mmol) added by portions with stirring. The reaction was stirred for 23 hours to afford complete conversion to the desired product. The pure acid was obtained following RP-HPLC in good yield.

(Step 4b) Synthesis of Chelator 1A

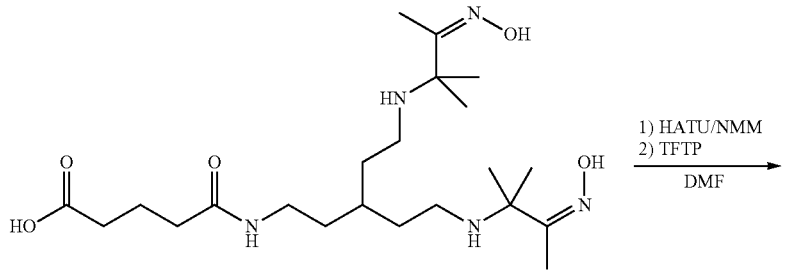

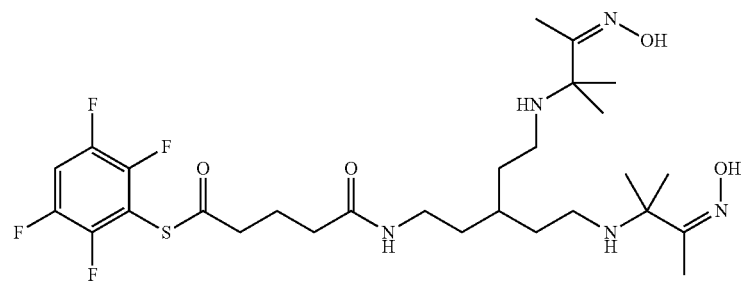

Chelator 1A

To [Chelator 1]-glutaric acid (from Step 4a; 300 mg, 0.66 mmol) in DMF (2 ml) was added HATU (249 mg, 0.66 mmol) and NMM (132 µL, 1.32 mmol). The mixture was stirred for 5 minutes then tetrafluorothiophenol (0.66 mmol, 119 mg) was added. The solution was stirred for 10 minutes then the reaction mixture was diluted with 20% acetonitrile/water (8 ml) and the product purified by RP-HPLC yielding 110 mg of the desired product following freeze-drying.

Example 5

Synthesis of disulfide [Cys$^{2-6}$] thioether cyclo [CH$_2$CO-Lys(Chelator 1-glutaryl)-Cys$^2$-Arg-Gly-Asp-Cys$^6$-Phe-Cys]-NH$_2$

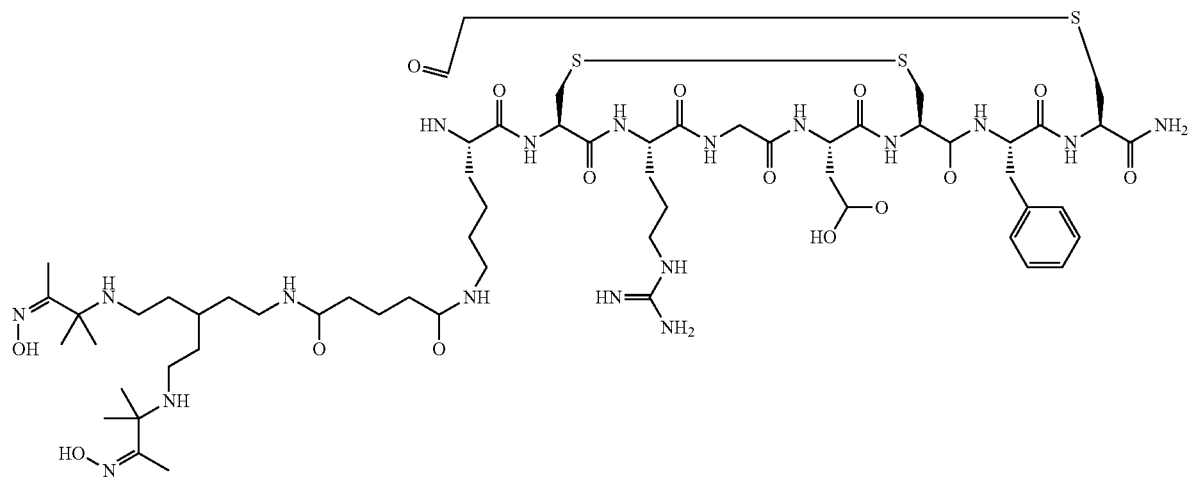

Molecular Weight = 1407.754
Exact Mass = 1406.662
Molecular Formula = C60H98N18O15S3

(Step 5a) Synthesis of ClCH$_2$CO-Lys-Cys(tBu)-Arg-Gly-Asp-Cys(tBu)-Phe-Cys-NH$_2$

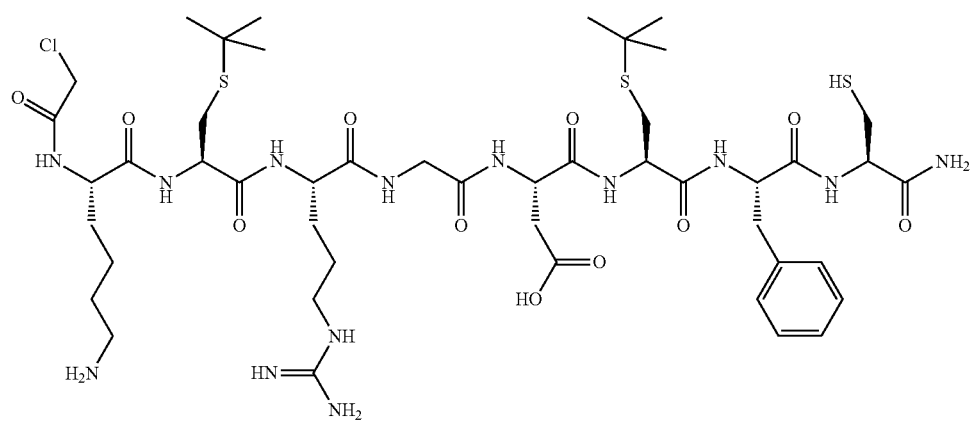

Molecular Weight = 1118.844
Exact Mass = 1117.464
Molecular Formula = C46H76ClN13O11S3

The peptide was synthesised on an ABI 433A automatic peptide synthesiser starting with Rink Amide AM resin on a 0.25 mmol scale using 1 mmol amino acid cartridges. The amino acids were pre-activated using HBTU before coupling. N-terminal amine groups were chloroacetylated using a solution of chloroacetic anhydride in DMF for 30 min. The simultaneous removal of peptide and side-chain protecting groups (except tBu) from the resin was carried out in TFA containing TIS (5%), $H_2O$ (5%) and phenol (2.5%) for two hours. After work-up 295 mg of crude peptide was obtained (Analytical HPLC: Gradient, 5-50% B over 10 min where A=$H_2O$/0.1% TFA and B=$CH_3CN$/0.1% TFA; column, Phenomenex Luna 3μ C18 (2) 50×4.6 mm; flow, 2 ml/min; detection, UV 214 nm; product retention time, 6.42 min). Further product characterisation was carried out using mass spectrometry: Expected, M+H at 1118.5, found, at 1118.6).

(Step 5b) Synthesis of thioether cyclo[$CH_2$CO-Lys-Cys(tBu)-Arg-Gly-Asp-Cys(tBu)-Phe-Cys]-$NH_2$

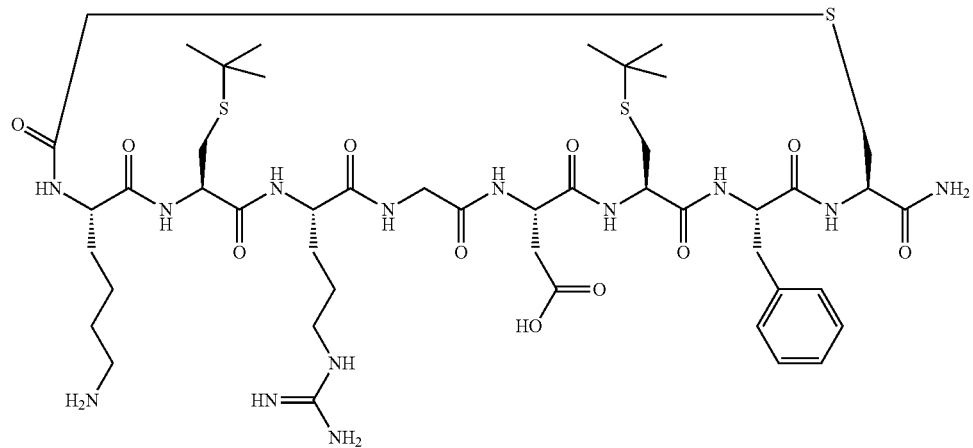

Molecular Weight = 1082.383
Exact Mass = 1081.487
Molecular Formula = C46H75N13O11S3

295 mg of ClCH$_2$CO-Lys-Cys(tBu)-Arg-Gly-Asp-Cys(tBu)-Phe-Cys-NH$_2$ was dissolved in water/acetonitrile. The mixture was adjusted to pH 8 with ammonia solution and stirred for 16 hours. After work-up 217 mg of crude peptide was obtained (Analytical HPLC: Gradient, 5-50% B over 10 min where A=H$_2$O/0.1% TFA and B=CH$_3$CN/0.1% TFA; column, Phenomenex Luna 3μ C18 (2) 50×4.6 mm; flow, 2 ml/min; detection, UV 214 nm; product retention time, 6.18 min). Further product characterisation was carried out using mass spectrometry: Expected, M+H at 1882.5, found, at 1882.6).

(Step 5c) Synthesis of disulfide [Cys$^{2-6}$] thioether cyclo[CH$_2$CO-Lys-Cys$^2$-Arg-Gly-Asp-Cys$^6$-Phe-Cys]-NH$_2$

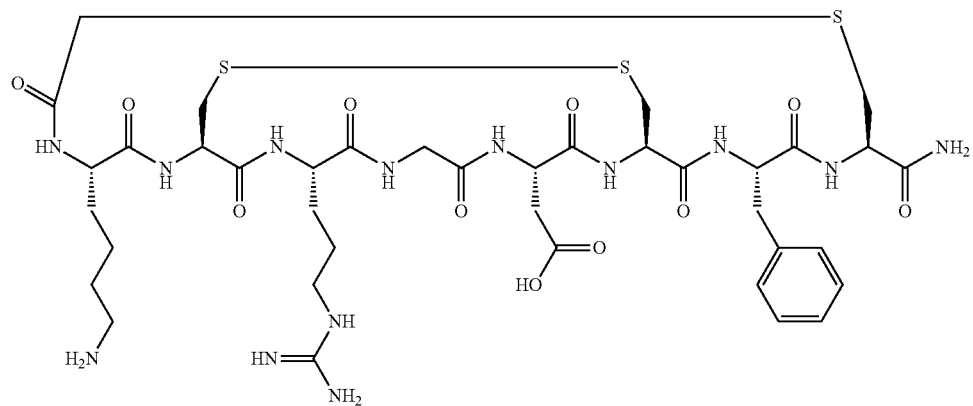

Molecular Weight = 968.150
Exact Mass = 967.346
Molecular Formula = C38H57N13O11S3

217 mg of thioether cyclo[CH$_2$CO-Lys-Cys(tBu)-Arg-Gly-Asp-Cys(tBu)-Phe-Cys]-NH$_2$ was treated with a solution of anisole (500 μL), DMSO (2 ml) and TFA (100 ml) for 60 min following which the TFA was removed in vacuo and the peptide precipitated by the addition of diethyl ether. Purification by preparative HPLC (Phenomenex Luna 10μ C18 (2) 250×50 mm column) of the crude material (202 mg) was carried out using 0-30% B, where A=H$_2$O/0.1% TFA and B=CH$_3$CN/0.1% TFA, over 60 min at a flow rate of 50 ml/min. After lyophilisation 112 mg of pure material was obtained (Analytical HPLC: Gradient, 5-50% B over 10 min where A=H$_2$O/0.1% TFA and B=CH$_3$CN/0.1% TFA; column, Phenomenex Luna 3μ C18 (2) 50×4.6 mm; flow, 2 ml/min; detection, UV 214 nm; product retention time, 5.50 min). Further product characterisation was carried out using mass spectrometry: Expected, M+H at 968, found, at 971).

(Step 5d) Synthesis of disulfide [Cys$^{2-6}$] thioether cyclo[CH$_2$CO-Lys(Chelator 1-glutaryl)-Cys$^2$-Arg-Gly-Asp-Cys$^6$-Phe-Cys]-NH$_2$

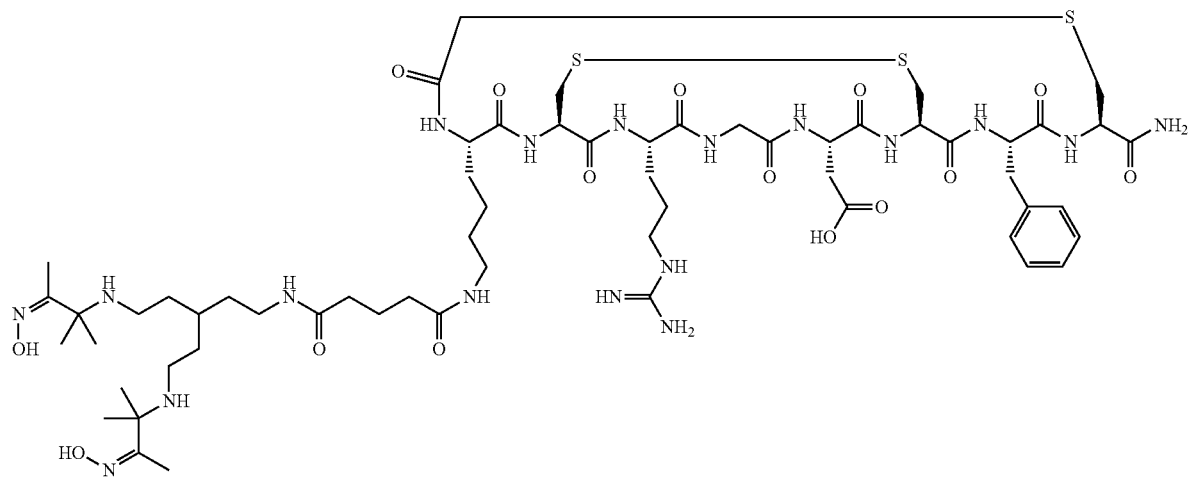

Molecular Weight = 1407.754
Exact Mass = 1406.662
Molecular Formula = C60H98N18O15S3

9.7 mg of disulfide[Cys$^{2-6}$] thioether cyclo[CH$_2$CO-Lys-Cys-Arg-Gly-Asp-Cys-Phe-Cys]-NH$_2$, 9.1 mg of Chelator 1A (Example 5) and 6 μL of NMM was dissolved in DMF (0.5 ml). The mixture was stirred for 3 hours. Purification by preparative HPLC (Phenomenex Luna 5μ C18 (2) 250× 21.20 mm column) of the reaction mixture was carried out using 0-30% B, where A=H$_2$O/0.1% TFA and B=CH$_3$CN/ 0.1% TFA, over 40 min at a flow rate of 10 ml/min. After lyophilisation 5.7 mg of pure material was obtained (Analytical HPLC: Gradient, 0-30% B over 10 min where A=H$_2$O/0.1% TFA and B=CH$_3$CN/0.1% TFA; column, Phenomenex Luna 3μ C18 (2) 50×4.6 mm; flow, 2 ml/min; detection, UV 214 nm; product retention time, 7.32 min). Further product characterisation was carried out using mass spectrometry: Expected, M+H at 1407.7, found, at 1407.6).

Example 6

Synthesis of disulfide [Cys$^{2-6}$] thioether cyclo [CH$_2$CO-Lys(Chelator 1-glutaryl)-Cys$^2$-Arg-Gly-Asp-Cys$^6$-Phe-Cys]-(PEG)$_3$-NH$_2$ (Maraciclatide)

(Step 6a) Synthesis of 17-(Fmoc-amino)-5-oxo-6-aza-3,9,12,15-tetraoxaheptadecanoic acid

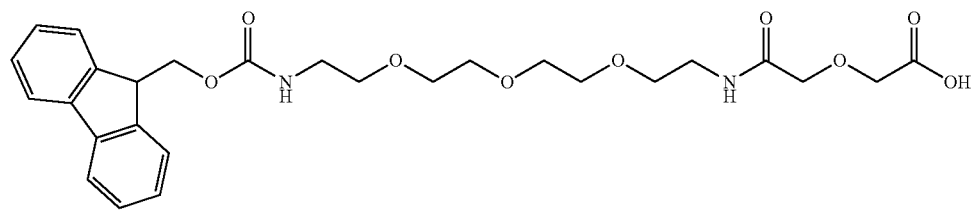 [SMILES: O=C(O)COCC(=O)NCCOCCOCCOCCNC(=O)OCC1c2ccccc2-c2ccccc21]

This building block is coupled to the solid-phase using Fmoc chemistry.

1,11-Diazido-3,6,9-trioxaundecane

A solution of dry tetraethyleneglycol (19.4 g, 0.100 mol) and methanesulfonyl chloride (25.2 g, 0.220 mol) in dry THF (100 ml) was kept under argon and cooled to 0° C. in an ice/water bath. To the flask was added a solution of triethylamine (22.6 g, 0.220 mol) in dry THF (25 ml) dropwise over 45 min. After 1 hr the cooling bath was removed and stirring was continued for 4 hrs. Water (60 ml) was added. To the mixture was added sodium hydrogen carbonate (6 g, to pH 8) and sodium azide (14.3 g, 0.220 mmol), in that order. THF was removed by distillation and the aqueous solution was refluxed for 24 h (two layers formed). The mixture was cooled and ether (100 ml) was added. The aqueous phase was saturated with sodium chloride. The phases were separated and the aqueous phase was extracted with ether (4×50 ml). Combined organic phases were washed with brine (2×50 ml) and dried (MgSO$_4$). Filtration and concentration gave 22.1 g (91%) of yellow oil. The product was used in the next step without further purification.

11-Azido-3,6,9-trioxaundecanamine

To a mechanically, vigorously stirred suspension of 1,11-diazido-3,6,9-trioxaundecane (20.8 g, 0.085 mol) in 5% hydrochloric acid (200 ml) was added a solution of triphenylphosphine (19.9 g, 0.073 mol) in ether (150 ml) over 3 hrs at room temperature. The reaction mixture was stirred for additional 24 hrs. The phases were separated and the aqueous phase was extracted with dichloromethane (3×40 ml). The aqueous phase was cooled in an ice/water bath and pH was adjusted to ca 12 by addition of KOH. The product was extracted into dichloromethane (5×50 ml). Combined organic phases were dried (MgSO$_4$). Filtration and evaporation gave 14.0 g (88%) of yellow oil. Analysis by MALDI-TOF mass spectroscopy (matrix: α-cyano-4-hydroxycinnamic acid) gave a M+H peak at 219 as expected. Further characterisation using $^1$H (500 MHz) and $^{13}$C (125 MHz) NMR spectroscopy verified the structure.

17-Azido-5-oxo-6-aza-3,9,12,15-tetraoxaheptadecanoic acid

To a solution of 11-azido-3,6,9-trioxaundecanamine (10.9 g, 50.0 mmol) in dichloromethane (100 ml) was added diglycolic anhydride (6.38 g, 55.0 mmol). The reaction mixture was stirred overnight. HPLC analysis (column Vydac 218TP54; solvents: A=water/0.1% TFA and B=acetonitrile/0.1% TFA; gradient 4-16% B over 20 min; flow 1.0 ml/min; UV detection at 214 and 284 nm), showed complete conversion of starting material to a product with retention time 18.3 min. The solution was concentrated to give quantitative yield of a yellow syrup. The product was analysed by LC-MS (ES ionisation) giving [MH]+ at 335 as expected. $^1$H (500 MHz) and $^{13}$C (125 MHz) NMR spectroscopy was in agreement with structure The product was used in the next step without further purification.

17-Amino-5-oxo-6-aza-3,9,12,15-tetraoxaheptadecanoic acid

A solution of 17-azido-5-oxo-6-aza-3,9,12,15-tetraoxaheptadecanoic acid (8.36 g, 25.0 mmol) in water (100 ml) was reduced using $H_2(g)$-Pd/C (10%). The reaction was run until LC-MS analysis showed complete conversion of starting material (column Vydac 218TP54; solvents: A=water/0.1% TFA and B=acetonitrile/0.1% TFA; gradient 4-16% B over 20 min; flow 1.0 ml/min; UV detection at 214 and 284 nm, ES ionisation giving M+H at 335 for starting material and 309 for the product). The solution was filtered and used directly in the next step.

17-(Fmoc-amino)-5-oxo-6-aza-3,9,12,15-tetraoxaheptadecanoic acid

To the aqueous solution of 17-amino-5-oxo-6-aza-3,9,12,15-tetraoxaheptadecanoic acid from above (corresponding to 25.0 mmol amino acid) was added sodium bicarbonate (5.04 g, 60.0 mmol) and dioxan (40 ml). A solution of Fmoc-chloride (7.11 g, 0.275 mol) in dioxan (40 ml) was added dropwise. The reaction mixture was stirred overnight. Dioxan was evaporated off (rotavapor) and the aqueous phase was extracted with ethyl acetate. The aqueous phase was acidified by addition of hydrochloric acid and precipitated material was extracted into chloroform. The organic phase was dried (MgSO$_4$), filtered and concentrated to give 11.3 g (85%) of a yellow syrup. The structure was confirmed by LC-MS analysis (column Vydac 218TP54; solvents: A=water/0.1% TFA and B=acetonitrile/0.1% TFA; gradient 40-60% B over 20 min; flow 1.0 ml/min; UV detection at 214 and 254 nm, ES ionisation giving M+H at 531 as expected for the product peak at 5.8 minutes). The analysis showed very low content of side products and the material was used without further purification.

(Step 6b) Synthesis of ClCH$_2$CO-Lys-Cys(tBu)-Arg-Gly-Asp-Cys(tBu)-Phe-Cys-(PEG)$_3$-NH$_2$

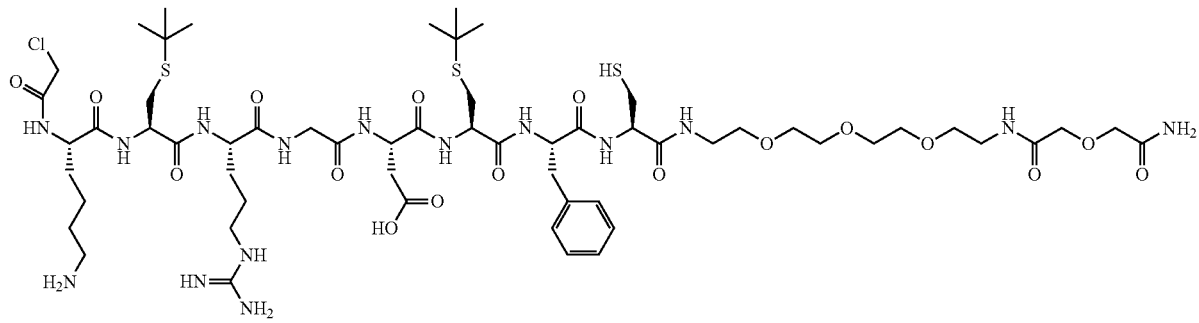

Molecular Weight = 1409.163
Exact Mass = 1407.612
Molecular Formula = C58H98ClN15O17S3

The PEG unit was coupled manually to Rink Amide AM resin, starting on a 0.25 mmol scale, mediated by HATU activation. The remaining peptide was assembled on an ABI 433A automatic peptide synthesiser using 1 mmol amino acid cartridges. The amino acids were pre-activated using HBTU before coupling. N-terminal amine groups were chloroacetylated using a solution of chloroacetic anhydride in DMF for 30 min.

The simultaneous removal of peptide and side-chain protecting groups (except tBu) from the resin was carried out in TFA containing TIS (5%), H$_2$O (5%) and phenol (2.5%) for two hours. After work-up 322 mg of crude peptide was obtained (Analytical HPLC: Gradient, 5-50% B over 10 min where A=H$_2$O/0.1% TFA and B=CH$_3$CN/0.1% TFA; column, Phenomenex Luna 3μ C18 (2) 50×4.6 mm; flow, 2 ml/min; detection, UV 214 nm; product retention time, 6.37 min). Further product characterisation was carried out using mass spectrometry: Expected, M+H at 1409, found, at 1415).

(Step 6c) Synthesis of thioether cyclo[CH$_2$CO-Lys-Cys(tBu)-Arg-Gly-Asp-Cys(tBu)-Phe-Cys]-(PEG)$_3$-NH$_2$

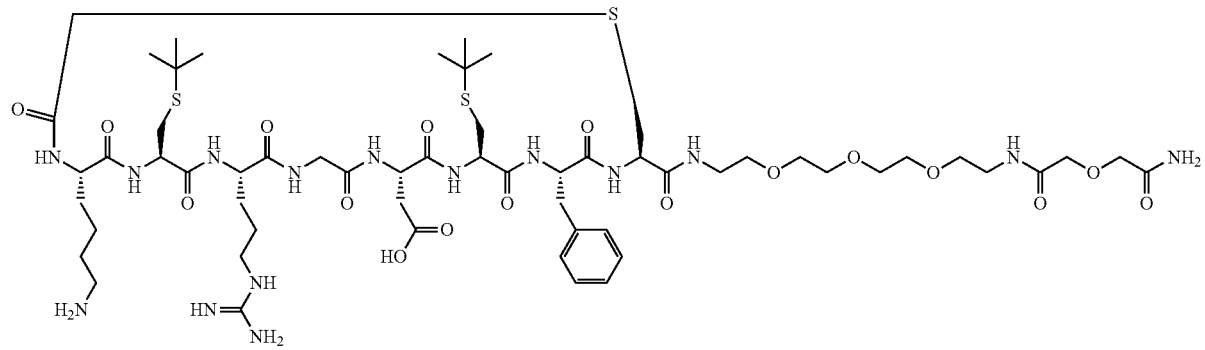

Molecular Weight = 1372.702
Exact Mass = 1371.635
Molecular Formula = C58H97N15O17S3

322 mg of ClCH$_2$CO-Lys-Cys(tBu)-Arg-Gly-Asp-Cys(tBu)-Phe-Cys-(PEG)$_3$-NH$_2$ was dissolved in water/acetonitrile. The mixture was adjusted to pH 8 with ammonia solution and stirred for 16 hours.

After work-up crude peptide was obtained (Analytical HPLC: Gradient, 5-50% B over 10 min where A=H$_2$O/0.1% TFA and B=CH$_3$CN/0.1% TFA; column, Phenomenex Luna 3μ C18 (2) 50×4.6 mm; flow, 2 ml/min; detection, UV 214 nm; product retention time, 6.22 min). Further product characterisation was carried out using mass spectrometry: Expected, M+H at 1373, found, at 1378).

(Step 6d) Synthesis of disulfide [Cys$^{2-6}$] thioether cyclo[CH$_2$CO-Lys-Cys$^2$-Arg-Gly-Asp-Cys$^6$-Phe-Cys]-(PEG)3-NH$_2$

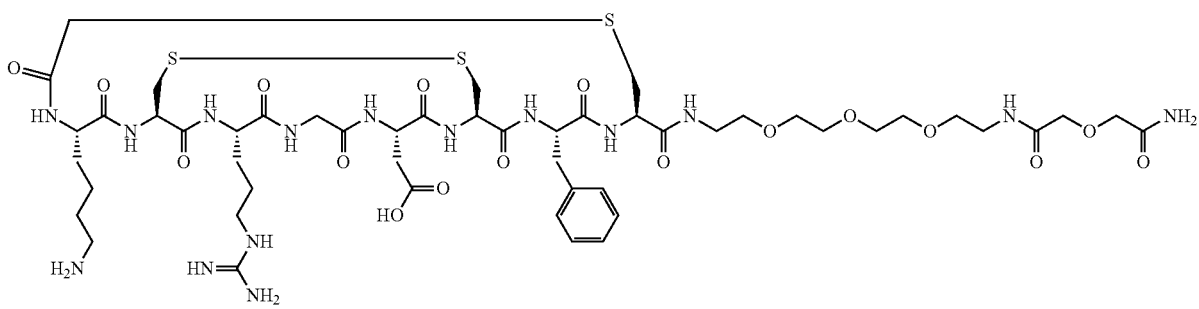

Molecular Weight = 1258.469
Exact Mass = 1257.494
Molecular Formula = C50H79N15O17S3

Thioether cyclo[CH$_2$CO-Lys-Cys(tBu)-Arg-Gly-Asp-Cys(tBu)-Phe-Cys]-(PEG)$_3$-NH$_2$ was treated with a solution of anisole (200 µL), DMSO (2 ml) and TFA (100 ml) for 60 min following which the TFA was removed in vacuo and the peptide precipitated by the addition of diethyl ether. Purification by preparative HPLC (Phenomenex Luna 5µ C18 (2) 250×21.20 mm column) of 70 mg crude material was carried out using 0-30% B, where A=H$_2$O/0.1% TFA and B=CH$_3$CN/0.1% TFA, over 40 min at a flow rate of 10 ml/min. After lyophilisation 46 mg of pure material was obtained (Analytical HPLC: Gradient, 0-30% B over 10 min where A=H$_2$O/0.1% TFA and B=CH$_3$CN/0.1% TFA; column, Phenomenex Luna 3µ C18 (2) 50×4.6 mm; flow, 2 ml/min; detection, UV 214 nm; product retention time, 6.80 min). Further product characterisation was carried out using mass spectrometry: Expected, M+H at 1258.5, found, at 1258.8).

(Step 6e) Synthesis of disulfide [Cys$^{2-6}$] thioether cyclo[CH$_2$CO-Lys(Chelator 1-glutaryl)-Cys$^2$-Arg-Gly-Asp-Cys$^6$-Phe-Cys]-(PEG)$_3$-NH$_2$

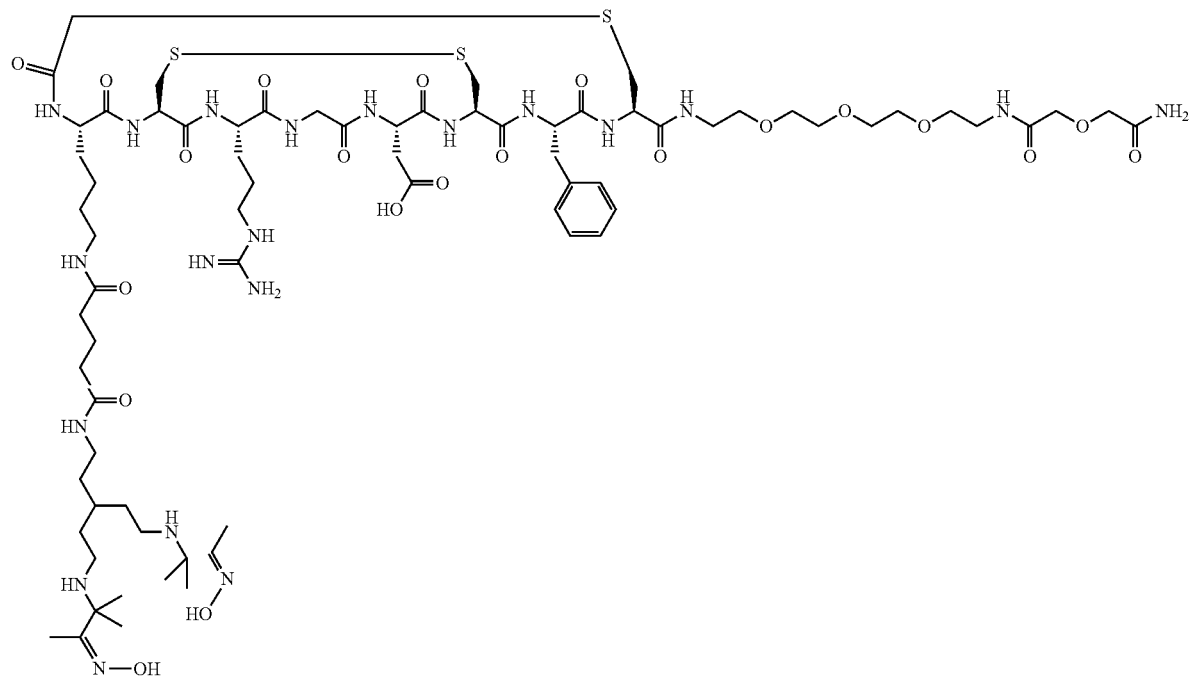

Molecular Weight = 1698.073
Exact Mass = 1696.810
Molecular Formula = C72H120N20O21S3

13 mg of [Cys$^{2-6}$] cyclo[CH$_2$CO-Lys-Cys-Arg-Gly-Asp-Cys-Phe-Cys]-(PEG)$_3$-NH$_2$, 9.6 mg of Chelator 1A and 8 µL of NMM was dissolved in DMF (0.5 ml). The mixture was stirred for 2 hours and 30 minutes. Purification by preparative HPLC (Phenomenex Luna 5µ C18 (2) 250×21.20 mm column) of the reaction mixture was carried out using 0-30% B, where A=H$_2$O/0.1% TFA and B=CH$_3$CN/0.1% TFA, over 40 min at a flow rate of 10 ml/min. After lyophilisation 14.2 mg of pure material was obtained (Analytical HPLC: Gradient, 0-30% B over 10 min where A=H$_2$O/0.1% TFA and B=CH$_3$CN/0.1% TFA; column, Phenomenex Luna 3µ C18 (2) 50×4.6 mm; flow, 2 ml/min; detection, UV 214 nm; product retention time, 7.87 min). Further product characterisation was carried out using mass spectrometry: Expected, M+H at 1697.8, found, at 1697.9).

Example 7: Choice of Radioprotectant

The effect, on radiolabelling efficiency and radiostabilisation, of three radioprotectants, pABA, gentisic acid and ascorbic acid, was evaluated for freeze-dried kits. The formulations were identical to Formulation A (see Example 9) except for the addition of the radioprotectant and an increased amount of sodium carbonate to maintain the pH close to 9.3, see Table 2:

TABLE 2

| radioprotectant formulations | | | |
|---|---|---|---|
| pABA, µg per vial | Gentisic acid, µg per vial | Ascorbic acid, µg per vial | Sodium carbonate, µg per vial |
| 350 | — | — | 830 |
| — | 1000 | — | 1530 |
| — | — | 500 | 930 |

Formulation A had an RCP at 20 minutes post-reconstitution of ca. 90-91%, falling to 82-85% at 4-hours, and 75-82% at 8-hours post-reconstitution.

The freeze-dried kits containing ascorbic acid had a poor radiolabelling efficiency—the RCP was 80% at both 20 minutes and 4 hours post-reconstitution.

The freeze-dried kits with gentisic acid showed a good radiolabelling efficiency, 94% at 20 minutes post reconstitution and a good radiostabilising effect, the RCP was 90% at 4 hours post reconstitution. However, the reconstituted kit solution discoloured (turned pink) after some time. Similar discolouration was observed in solution chemistry experiments.

The freeze-dried kits with pABA showed a good radiolabelling efficiency and the RCP was stabilised. The RCP values were approximately 90% at both 20 minutes and 4 hours post reconstitution, with stability maintained even at 8-hours post reconstitution (see Example 8). No new radioactive impurities were observed compared to Formulation A.

Example 8: Optimisation of Amount of Radioprotectant

To optimise the amount of pABA in the formulation, a factorial design with 3 levels of pABA [100 to 600 µg per vial] and 2 levels of pH [8.7 to 9.3] was prepared. The levels of other kit components were as for Formulation A. The sodium carbonate levels were used to adjust the pH.

TABLE 3

| RCP results from pABA optimisation study | | | | | |
|---|---|---|---|---|---|
| | pABA | Na$_2$CO$_3$ | | % RCP (at time p.r.) | |
| Formulation | (µg/vial) | (µg/vial) | pH | 20 min | 4 hours | 8 hours |
| #1 | 100 | 300 | 8.9 | 89.2 | 88.0 | 86.3 |
| #2 | 100 | 600 | 9.3 | 91.6 | 88.8 | 85.8 |
| #3 | 300 | 600 | 9.1 | 93.1 | 92.1 | 90.5 |
| #4 | 350 | 500 | 8.9 | 89.6 | 89.9 | 88.6 |
| #5 | 350 | 630 | 9.0 | 91.6 | 91.6 | 90.8 |
| #6 | 350 | 830 | 9.2 | 91.8 | 90.7 | 89.5 |
| #7 | 600 | 680 | 8.9 | 88.4 | 89.3 | 88.7 |
| #8 | 600 | 1000 | 9.1 | 91.7 | 91.8 | 90.5 | pr = post-reconstitution

Analysing the results from the factorial design, shown in Table 3, showed that the optimal pABA amount with respect to initial RCP and radiostabilising capacity is between 200 and 350 µg/vial Two further batches with respectively 200 µg (Batch #9; 630 µg Na$_2$CO$_3$ pH 9.3) and 300 µg (Batch #10; 800 µg Na$_2$CO$_3$ pH 9.3) pABA, gave very similar RCP values at an initial time point and during stability. The results showed that there was no significant difference between freeze dried kits containing 200 and 300 µg pABA with respect to radiolabelling efficiency or radiostabilising capacity.

Example 9: Comparative Lyophilised Kit Formulations

Lyophilised kits were prepared as follows, to compare the prior art kit of Edwards et al [Nucl. Med. Biol., 35, 365-375 (2008)] and the stabilised kit of the present invention:

TABLE 1

| kit formulations | | |
|---|---|---|
| Component | Formulation A Quantity per vial (µg) | Formulation C Quantity per vial (µg) |
| Maraciclatide | 75 | 75 |
| Stannous chloride dihydrate | 17.8 | 17.8 |
| Methylene diphosphonic acid sodium salt | 90 | 90 |
| Para-amino-benzoic acid (pABA) sodium salt | 0 | 200 |
| Sodium hydrogen carbonate | 1800 | 1800 |
| Sodium carbonate anhydrous | 530 | 630 |

Example 10: Generator Compatibility Study

Two generator compatibility studies have been performed to investigate the compatibility of Formulation C. The generators studied in the first study were: Technelite Technetium-99m, Sterile generator [Bristol Myers Squibb Medical Imaging], Drytec Technetium-99m, Sterile generator [GE Heathcare, UK], Ultra-Technekow® DTE generator [Tyco Healthcare Mallinckrodt, USA] and ISOTEC Mo-99-Tc-99m, Sterile generator [Amersham Health, Norway]. The test samples were Formulation C (Batch #9 of Example 8). All samples were reconstituted with generator eluate of 3.1 GBq/6 ml. The variables studied for the generators were generator age (time between elutions) and eluate age (time after elution).

All four generators tested in this first study were compatible with Formulation C. There was only a small difference in the RCP values, 1.6%. The eluate age had a negative effect on both RCP and post reconstitution stability for all four generators.

Example 11: Stability of Freeze-Dried Kits

Shelf-life stability testing was performed on several batches of kit stored at various temperatures [−20° C., 5° C. and 25° C.], and for some temperatures up to 12 months. The RCP was determined after storage under different temperature conditions.

Formulation A kit.

5° storage 12 months: RCP at 4 hours post-reconstitution was 87%

25° storage 3 months: RCP at 4 hours post-reconstitution was 87%

Formulation C kit

5° storage 12 months: RCP at 4 hours post-reconstitution was 91.7%

25° storage 3 months: RCP at 4 hours post-reconstitution was 91.5%

25° storage 6 months: RCP at 4 hours post-reconstitution was >90%

Formulation C has a shelf-life of at least 50 months when stored at 5° C., whereas Formulation A would have to be stored at −20° C. to ensure adequate kit RCP performance.

The invention claimed is:

1. A stabilized non-radioactive kit for the preparation of a $^{99m}$Tc-maraciclatide radiopharmaceutical composition, said kit comprising:
   (a) maraciclatide;
   (b) para-aminobenzoic acid sodium salt in an amount between 100 to 600 μg;
   (c) stannous chloride dihydrate;
   (d) methylene diphosphonic acid;
   (e) a buffer comprising sodium hydrogen carbonate in an amount of approximately 1800 μg; and
   wherein all the components of said kit are lyophilized and stored in a single container; and
   wherein the components are present in an amount such that reconstitution in sterile water for injection produces a composition with a pH between 6.5 and 9.5.

2. The kit according to claim 1, wherein the para-aminobenzoic acid sodium salt is present an amount between 200 to 350 μg.

3. The kit according to claim 1, which does not include a sugar or sugar alcohol.

4. The kit according to claim 1, wherein the para-aminobenzoic acid sodium salt is present in an amount from 2⅔ times to about 4⅔ times by weight compared to the maraciclatide.

5. The kit according to claim 1, wherein the buffer comprises sodium carbonate in an amount of approximately 300 to 1,000 μg.

6. The kit according to claim 1, wherein the components are present in an amount such that reconstitution in sterile water for injection produces a composition with a pH between 8.7 and 9.3.

7. The kit according to claim 1, wherein the buffer comprises sodium carbonate in an amount from approximately 530 to 630 μg.

8. The kit according to claim 1, wherein the maraciclatide is present in an amount of approximately 75 μg.

9. The kit according to claim 1, wherein the stannous chloride dihydrate in an amount of approximately 17.8 μg.

10. The kit according to claim 1, wherein the methylene diphosphonic acid in an amount of approximately 90 μg.

11. A stabilized non-radioactive kit for the preparation of a $^{99m}$Tc-maraciclatide radiopharmaceutical composition, said kit comprising:
   (a) maraciclatide;
   (b) para-aminobenzoic acid sodium salt in an amount between 100 to 600 μg;
   (c) stannous chloride dihydrate;
   (d) methylene diphosphonic acid;
   (e) a buffer; and
   wherein all the components of said kit are lyophilized and stored in a single container, wherein the buffer comprises sodium hydrogen carbonate in an amount of approximately 1800 μg, and anhydrous sodium carbonate in an amount of approximately 530-630 μg.

12. A stabilized non-radioactive kit for the preparation of a $^{99m}$Tc-maraciclatide radiopharmaceutical composition, said kit comprising:
   (a) maraciclatide;
   (b) para-aminobenzoic acid sodium salt in an amount from 2⅔ times to about 4⅔ times by weight compared to the maraciclatide;
   (c) stannous chloride;
   (d) methylene diphosphonic acid;
   (e) a buffer comprising sodium hydrogen carbonate in an amount of approximately 1800 μg; and
   wherein all the components of said kit are lyophilized and stored in a single container; and
   wherein the components are present in an amount such that reconstitution in sterile water for injection produces a composition with a pH between 6.5 and 9.5.

13. The kit according to claim 12, wherein the components are present in an amount such that reconstitution produces a composition with a pH between 8.7 and 9.3.

14. The kit according to claim 12, wherein the para-aminobenzoic acid sodium salt is present an amount between 100 to 600 μg.

15. The kit according to claim 12, wherein the para-aminobenzoic acid sodium salt is present an amount between 200 to 350 μg.

16. The kit according to claim 12, wherein the buffer comprises sodium carbonate in an amount of approximately 300 to 1,000 μg.

17. The kit according to claim 12, wherein the buffer comprises sodium carbonate in an amount from approximately 530 to 630 μg.

18. The kit according to claim 12, wherein the components are present in an amount such that reconstitution produces a composition with a pH between 8.7 and 9.3.

* * * * *